US010345203B2

(12) United States Patent
Knorr et al.

(10) Patent No.: US 10,345,203 B2
(45) Date of Patent: Jul. 9, 2019

(54) TISSUE CASSETTE WITH BIASING ELEMENT

(71) Applicant: Leica Biosystems Nussloch GmbH, Nussloch (DE)

(72) Inventors: Stella Knorr, Brighton (AU); Andrew Guy, Coburg (AU); Ralf Eckert, Schriesheim (DE); Fiona Tarbet, Box Hill (AU); Fernando Dias, Endeavor Hills (AU); Chris Ryan, East Brunswick (AU); Neil Sanut, Pakenham (AU)

(73) Assignee: Leica Biosystems Nussloch GmbH, Nußloch (DE)

(*) Notice: Subject to any disclaimer, the term of this patent is extended or adjusted under 35 U.S.C. 154(b) by 0 days.

(21) Appl. No.: 15/091,653

(22) Filed: Apr. 6, 2016

(65) Prior Publication Data

US 2016/0216176 A1 Jul. 28, 2016

Related U.S. Application Data

(63) Continuation of application No. 14/204,375, filed on Mar. 11, 2014, now Pat. No. 9,389,154.

(Continued)

(51) Int. Cl.
*G01N 1/31* (2006.01)
*G01N 1/36* (2006.01)
*B01L 3/00* (2006.01)

(52) U.S. Cl.
CPC .............. *G01N 1/31* (2013.01); *B01L 3/508* (2013.01); *B01L 3/5457* (2013.01); *G01N 1/36* (2013.01);

(Continued)

(58) Field of Classification Search
CPC .......... B01L 2200/14; B01L 2300/021; B01L 2300/043; B01L 2300/0609;
(Continued)

(56) References Cited

U.S. PATENT DOCUMENTS 4,735,794 A   4/1988 Parkinson
4,801,553 A   1/1989 Owen et al.
(Continued)

FOREIGN PATENT DOCUMENTS

DE   102007011329 A1   9/2008
DE   102008005265 A1   7/2009
(Continued)

OTHER PUBLICATIONS

Communication dated Jul. 28, 2017, issued by the European Patent Office in counterpart European Application No. 14159645.2-2778654.
(Continued)

*Primary Examiner* — Samuel P Siefke
(74) *Attorney, Agent, or Firm* — Sughrue Mion, PLLC

(57) ABSTRACT

An apparatus for holding a tissue sample including a retaining member having a first tissue engaging surface and at least one biasing element, the first tissue engaging surface being moveably attached to the retaining member by said biasing element; and a base having a second tissue engaging surface and configured to engage the retaining member to form an interior area with the first and second tissue engaging surfaces facing each other, wherein the at least one biasing element urges the first tissue engaging surface toward the second tissue engaging surface to retain the tissue sample therebetween in the interior area.

34 Claims, 11 Drawing Sheets

Related U.S. Application Data

(60) Provisional application No. 61/798,728, filed on Mar. 15, 2013.

(52) U.S. Cl.
CPC ..... *B01L 2200/14* (2013.01); *B01L 2300/021* (2013.01); *B01L 2300/043* (2013.01); *B01L 2300/0609* (2013.01); *B01L 2300/12* (2013.01); *B01L 2300/123* (2013.01); *G01N 2001/315* (2013.01); *G01N 2001/366* (2013.01)

(58) Field of Classification Search
CPC .......... B01L 2300/12; B01L 2300/123; B01L 3/508; B01L 3/5457; G01N 1/31; G01N 1/36
See application file for complete search history.

(56) References Cited

U.S. PATENT DOCUMENTS

| | | | |
|---|---|---|---|
| 5,269,671 A | 12/1993 | McCormick | |
| 5,401,625 A | 3/1995 | Robinson | |
| 5,447,841 A | 9/1995 | Gray et al. | |
| 5,601,650 A | 2/1997 | Goldbecker et al. | |
| 5,695,942 A | 10/1997 | Farmilo et al. | |
| 5,817,032 A | 10/1998 | Williamson et al. | |
| 5,895,628 A | 4/1999 | Heid et al. | |
| 5,965,454 A | 10/1999 | Farmilo et al. | |
| 5,968,436 A | 10/1999 | Takezaki | |
| 6,042,874 A | 3/2000 | Visinoni et al. | |
| 6,103,518 A | 8/2000 | Leighton | |
| 6,207,408 B1 | 3/2001 | Essenfeld et al. | |
| 6,311,945 B1 | 11/2001 | DAngelo | |
| 6,329,645 B2 | 12/2001 | Giberson et al. | |
| 6,372,512 B1 | 4/2002 | Kerschmann | |
| 6,383,801 B1 | 5/2002 | Leighton | |
| 6,444,170 B1 | 9/2002 | Heid et al. | |
| 6,465,245 B1 | 10/2002 | Walton et al. | |
| 6,468,783 B1 | 10/2002 | Leighton | |
| 6,513,803 B2 | 2/2003 | Morales et al. | |
| 6,521,186 B1 | 2/2003 | Izvoztchikov et al. | |
| 6,586,713 B2 | 7/2003 | Essenfeld et al. | |
| 6,596,479 B1 | 7/2003 | Gray et al. | |
| 6,793,890 B2 | 9/2004 | Morales et al. | |
| 6,797,928 B2 | 9/2004 | Giberson et al. | |
| 6,803,018 B1 | 10/2004 | Stiller | |
| 6,815,199 B1 * | 11/2004 | Kubota | G01N 1/36 220/305 |
| 6,875,583 B2 | 4/2005 | Giberson et al. | |
| 6,902,928 B2 | 7/2005 | Izvortchikov et al. | |
| 6,991,934 B2 | 1/2006 | Walton et al. | |
| 7,005,110 B2 | 2/2006 | Taft et al. | |
| 7,075,045 B2 | 7/2006 | Visinoni | |
| 7,155,050 B1 | 12/2006 | Sloge et al. | |
| 7,156,814 B1 | 1/2007 | Williamson, IV et al. | |
| 7,179,424 B2 | 2/2007 | Williamson, IV et al. | |
| 7,217,392 B2 | 5/2007 | Bogen et al. | |
| 7,219,884 B2 | 5/2007 | Morales | |
| 7,273,587 B1 | 9/2007 | Birkner et al. | |
| 7,273,720 B1 | 9/2007 | Birkner et al. | |
| 7,329,533 B2 | 2/2008 | Fredenburgh | |
| 7,470,401 B2 | 12/2008 | Morales | |
| 7,521,021 B2 | 4/2009 | McCormick | |
| 7,526,987 B2 | 5/2009 | Morales | |
| 7,544,953 B2 | 6/2009 | Goodman | |
| 7,547,538 B2 | 6/2009 | Morales et al. | |
| 7,553,672 B2 | 6/2009 | Bogen et al. | |
| 7,575,556 B2 | 8/2009 | Speeg et al. | |
| 7,576,307 B2 | 8/2009 | Yazdanfar et al. | |
| 7,584,019 B2 | 9/2009 | Feingold et al. | |
| 7,593,787 B2 | 9/2009 | Feingold et al. | |
| 7,603,201 B2 | 10/2009 | Feingold et al. | |
| 7,618,828 B2 | 11/2009 | Bleuel et al. | |
| 7,657,070 B2 | 2/2010 | Lefebvre | |
| 7,663,101 B2 | 2/2010 | Goodman | |
| 7,666,620 B2 | 2/2010 | Wiederhold | |
| 7,687,255 B2 | 3/2010 | Chu | |
| 7,722,810 B2 | 5/2010 | Allen et al. | |
| 7,767,434 B2 | 8/2010 | Chu | |
| 7,776,274 B2 | 8/2010 | Williamson, IV et al. | |
| 7,780,919 B2 | 12/2010 | McCormick | |
| 7,850,912 B2 | 12/2010 | Favuzzi et al. | |
| 7,881,517 B2 | 2/2011 | Sloge et al. | |
| 7,888,132 B2 | 2/2011 | McCormick | |
| 7,901,634 B2 | 3/2011 | Testa | |
| 7,914,462 B2 | 3/2011 | Hutchins et al. | |
| 7,914,738 B2 | 3/2011 | Hutchins et al. | |
| 2005/0084425 A1 | 4/2005 | Williamson, IV et al. | |
| 2005/0112032 A1 | 5/2005 | McCormick | |
| 2005/0142631 A1 | 6/2005 | Mosconi et al. | |
| 2005/0147538 A1 | 7/2005 | Williamson, IV et al. | |
| 2006/0147896 A1 | 7/2006 | Schnetz et al. | |
| 2006/0177812 A1 | 8/2006 | Schnetz et al. | |
| 2006/0228772 A1 | 10/2006 | Donndelinger | |
| 2007/0072167 A1 | 3/2007 | Rochaix | |
| 2007/0104618 A1 | 5/2007 | Williamson, IV et al. | |
| 2007/0116612 A1 | 5/2007 | Williamson, IV | |
| 2007/0141711 A1 | 6/2007 | Stephens et al. | |
| 2007/0161609 A1 | 7/2007 | Buck et al. | |
| 2007/0166834 A1 | 7/2007 | Williamson, IV et al. | |
| 2007/0218542 A1 | 9/2007 | Li et al. | |
| 2008/0026366 A1 | 1/2008 | Harkins | |
| 2008/0138854 A1 | 6/2008 | Williamson | |
| 2008/0193014 A1 | 8/2008 | Ecker et al. | |
| 2008/0206807 A1 | 8/2008 | Duymelinck et al. | |
| 2008/0220468 A1 | 9/2008 | Windeyer et al. | |
| 2008/0227144 A1 | 9/2008 | Nightingale | |
| 2008/0254504 A1 | 10/2008 | Vom et al. | |
| 2008/0268496 A1 | 10/2008 | Mosconi et al. | |
| 2008/0274496 A1 | 11/2008 | Duymelinck et al. | |
| 2009/0098522 A1 | 4/2009 | Marcovitz | |
| 2009/0145920 A1 | 6/2009 | Kerrod et al. | |
| 2009/0165940 A1 | 7/2009 | Baur et al. | |
| 2009/0170152 A1 | 7/2009 | Reeser et al. | |
| 2009/0191544 A1 | 7/2009 | DeLa Torre Bueno | |
| 2009/0203066 A1 | 8/2009 | Perrut et al. | |
| 2009/0208105 A1 | 8/2009 | Bystrov et al. | |
| 2009/0222746 A1 | 9/2009 | Chirica et al. | |
| 2009/0253199 A1 | 10/2009 | McCormick | |
| 2010/0017030 A1 | 1/2010 | Feingold et al. | |
| 2010/0005563 A1 | 3/2010 | Konrad et al. | |
| 2010/0061632 A1 | 3/2010 | Young et al. | |
| 2010/0075410 A1 | 3/2010 | Desai et al. | |
| 2010/0092064 A1 | 4/2010 | Li | |
| 2010/0093023 A1 | 4/2010 | Gustafsson et al. | |
| 2010/0099140 A1 | 4/2010 | Donndelinger | |
| 2010/0112624 A1 | 5/2010 | Metzner et al. | |
| 2010/0112625 A1 | 5/2010 | Erben et al. | |
| 2010/0144002 A1 | 6/2010 | Donndelinger | |
| 2010/0167334 A1 | 7/2010 | Williamson, IV et al. | |
| 2010/0167338 A1 | 7/2010 | Amano et al. | |
| 2010/0182877 A1 | 7/2010 | Chu | |
| 2010/0184127 A1 | 7/2010 | Williamson, IV et al. | |
| 2010/0208955 A1 | 8/2010 | Mehes et al. | |
| 2010/0223935 A1 | 9/2010 | Donndelinger | |
| 2010/0248301 A1 | 9/2010 | Ulbrich et al. | |
| 2010/0278627 A1 | 11/2010 | Williamson, IV et al. | |
| 2010/0279341 A1 | 11/2010 | Steiner et al. | |
| 2010/0323395 A1 | 12/2010 | Ulbrich et al. | |
| 2010/0330660 A1 | 12/2010 | Hutchins et al. | |
| 2011/0008884 A1 | 1/2011 | Morales | |
| 2011/0034341 A1 | 2/2011 | Mehes et al. | |
| 2011/0045565 A1 | 2/2011 | Sanders et al. | |
| 2011/0054679 A1 | 3/2011 | Lefebvre et al. | |
| 2011/0060766 A1 | 3/2011 | Ehlke et al. | |
| 2011/0076753 A1 | 3/2011 | Goerner et al. | |

FOREIGN PATENT DOCUMENTS

| | | |
|---|---|---|
| DE | 102009010667 A1 | 9/2010 |
| DK | 1545775 T3 | 10/2010 |
| EP | 0807807 A1 | 11/1997 |

(56) References Cited

FOREIGN PATENT DOCUMENTS

| | | |
|---|---|---|
| EP | 1508026 A1 | 2/2005 |
| EP | 1682272 A2 | 7/2006 |
| EP | 1782737 A1 | 5/2007 |
| EP | 1782737 A1 | 9/2007 |
| EP | 1975595 A2 | 10/2008 |
| EP | 1985383 A1 | 10/2008 |
| EP | 2002894 A1 | 12/2008 |
| EP | 2091440 A1 | 8/2009 |
| WO | 00/05336 | 2/2000 |
| WO | 2004/028693 A1 | 4/2004 |
| WO | 2005/037182 A2 | 4/2005 |
| WO | 2008/073387 A1 | 6/2008 |
| WO | 2010/030358 A1 | 3/2010 |
| WO | 2010/085626 A1 | 7/2010 |
| WO | 2010/112316 A1 | 10/2010 |
| WO | 2011/041495 A1 | 4/2011 |

OTHER PUBLICATIONS

Communication dated Oct. 29, 2018 from the State Intellectual Property Office of the P.R.C. In counterpart Application No. 201710979969.1.

\* cited by examiner

TISSUE CASSETTE WITH BIASING ELEMENT

CROSS REFERENCE TO RELATED APPLICATIONS

This is a Continuation application of U.S. application Ser. No. 14/204,375 filed Mar. 11, 2014, which claims priority from U.S. Provisional Application 61/798,728 filed Mar. 15, 2013. The entire disclosures of the prior applications are considered part of the disclosure of the accompanying continuation application, and are hereby incorporated by reference.

BACKGROUND OF THE INVENTION

The present disclosure relates generally to a tissue cassette for retaining a tissue sample.

BACKGROUND

A biopsy is the removal of a tissue sample to examine tissue for signs of cancer or other disorders. Tissue samples are obtained in a variety of ways using various medical procedures involving a variety of the sample collection devices. For example, biopsies may be open (surgically removing tissue) or percutaneous (e.g. by fine needle aspiration, core needle biopsy or vacuum assisted biopsy).

After the tissue sample is collected, the tissue sample is analyzed at a lab (e.g. a pathology lab, biomedical lab, etc.) that is set up to perform the appropriate tests (such as histological analysis). Although this disclosure refers to a sample, it should be understood that the term sample can refer to one or more samples.

In order to properly process the tissue sample a series of steps may be performed including:
1. Grossing of the sample by cutting the sample to the proper size for analysis.
2. Fixing of the sample to immobilize molecular components and/or prevent degradation.
3. Embedding the sample in an embedding material, such as paraffin wax
4. Sectioning the embedded sample by using, for example, a microtome.

In conventional methods, the grossing step involves a lab technician cutting the tissue to the appropriate size for analysis and then placing the tissue in a tissue cassette. During the fixation stage, the cassettes are generally exposed to a fixing agent or chemical (e.g., a solution of formaldehyde in water such as formalin) shortly after sample collection. For example, U.S. Pat. No. 7,156,814 discloses a cassette which can withstand tissue preparation procedures.

After the tissue sample has been processed, the medical professional, in conventional methods, removes the tissue sample from the individual cassette to perform the embedding step. Specifically, the medical professional carefully orients the sample, based on the diagnostic view required, into a base mold containing an embedding material such as paraffin wax. Once the tissue is oriented properly in the base mold, the molten material is cooled to fully embed the tissue sample and hold it in the proper orientation. The paraffin is used to hold the sample in position while also providing a uniform consistency to further facilitate sectioning. While the term paraffin is used, this term is not limiting and describes an example of an embedding medium.

Then the sample is removed and sliced into a plurality of thin sections (e.g., 2 to 25µ thick sections), often using a microtome, for further processing and inspection. Such sectioning of the sample often helps a medical professional properly assess the sample under a microscope (e.g. diagnose relationships between cells and other constituents of the sample, or perform other assessments).

The current process requires human intervention at both the grossing and embedding steps. Such manual handling of the sample can increase the likelihood of mis-identifying the sample, cross contaminating the samples, or losing part or the entire sample. Additionally, the numerous steps of manual manipulation can often increase the time that it takes to provide a proper assessment for each sample, once the sample is collected.

SUMMARY OF THE INVENTION

This invention provides a device that allows for the tissue sample to be orientated during the grossing step and to remain in the same orientation through all steps to the embedding step. Through the multiple embodiments, the tissue sample cassette of this invention reduces the manual handling of the tissue samples. Example embodiments of this application may address one or more of the above identified issues. However, an embodiment of this application need not solve, address, or otherwise improve on existing technologies.

DETAILED DESCRIPTION OF THE INVENTION

In the following detailed description, reference will be made to the accompanying drawing(s), in which similar elements are designated with similar numerals. The aforementioned accompanying drawings show by way of illustration and not by way of limitation, specific example embodiments and implementations consistent with principles of an example embodiment. These implementations are described in sufficient detail to enable those skilled in the art to practice an example embodiment and it is to be understood that other implementations may be utilized and that structural changes and/or substitutions of various elements may be made without departing from the scope and spirit of an example embodiment. The following detailed description is, therefore, not to be construed in a limited sense.

Figure 1:
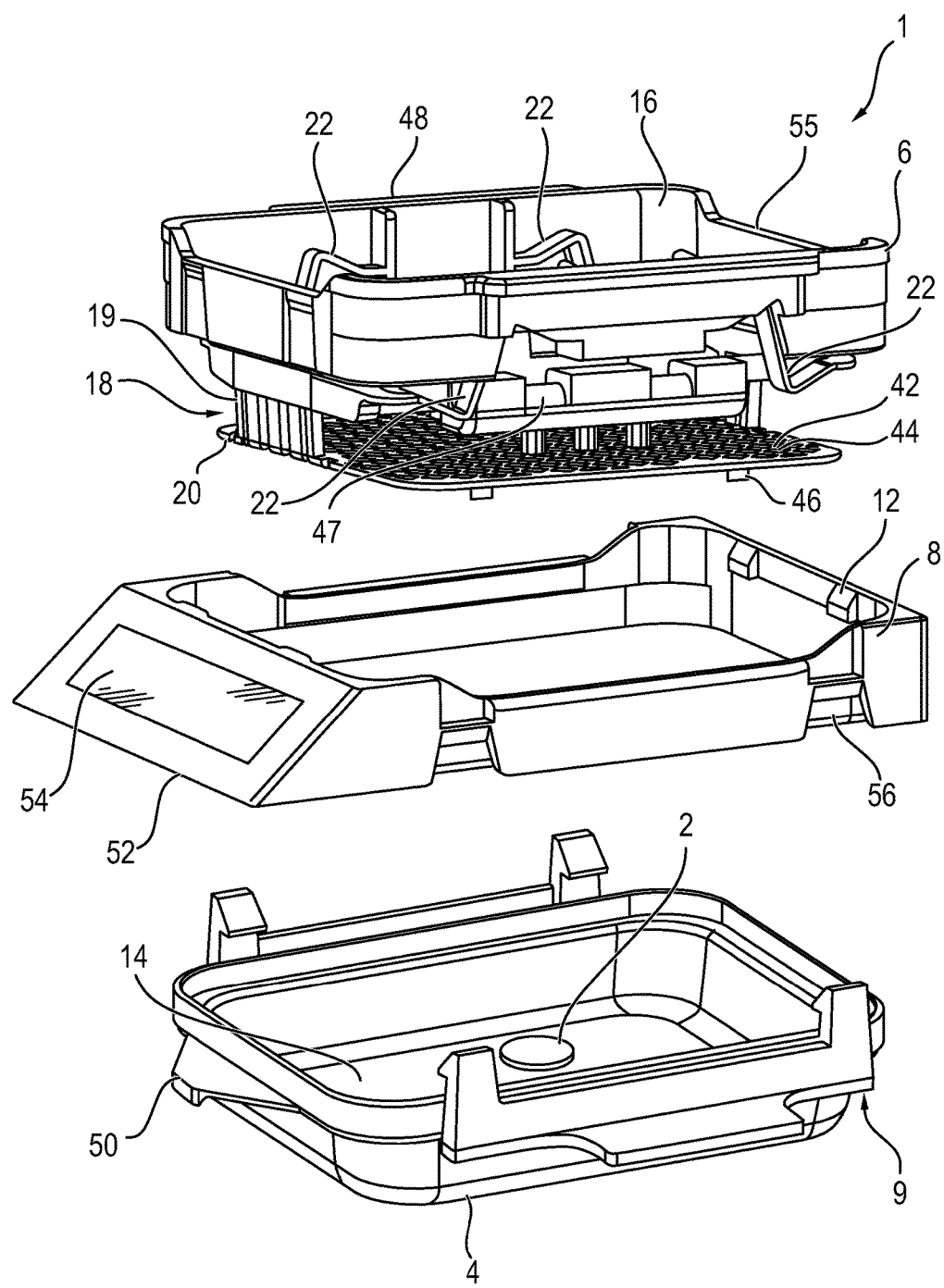
FIG. 1 is an exploded view of a tissue cassette according to a first embodiment in a non-assembled state.
Figure 2:
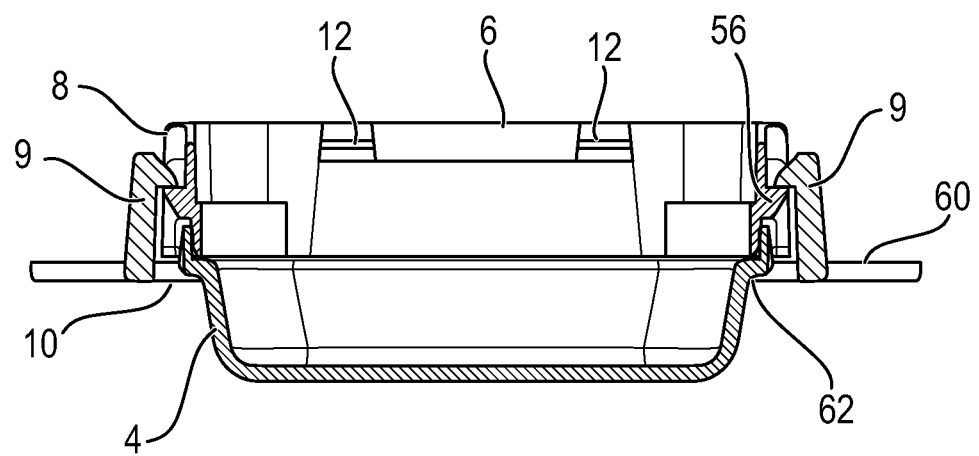
FIG. 2 shows an exterior sectional view the tissue cassette of FIG. 1 in an assembled state.
Figure 3:
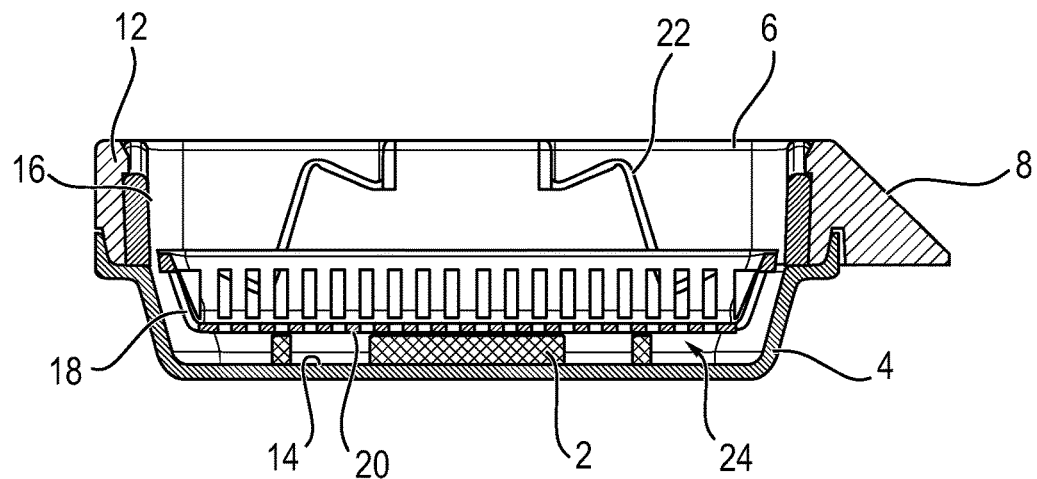
FIG. 3 shows an interior sectional view of the tissue cassette of FIG. 1 in an assembled state.

FIGS. 1-3 illustrate a tissue cassette 1 according to a first exemplary embodiment of the present application. The tissue cassette 1 retains a tissue sample 2 in the proper orientation to allow for the automation of the processing and a reduction in human error.

A tissue cassette 1, according to one embodiment of the invention, has a base 4 and a retaining member 6 which cooperate to retain the tissue sample 2, as discussed below. In addition, a frame 8 may optionally be provided to surround the outer perimeter of the retaining member 6. In this embodiment, the base 4 is connected to the frame 8 by latching member 9, and the frame 8 is connected to the retaining member 6 by a locking member 12. In this way, the retaining member 6 fits into the inside perimeter of the base 4 as shown in FIGS. 2-3. The base 4 may have a sealing member 10 which forms a liquid seal between the frame 8 and the base 4.

FIG. 3 shows the base 4 with a bottom surface which corresponds to a second tissue engaging surface 14. The retaining member 6 is formed with a rim portion 16 and a tissue retaining element 18 having a bottom surface corresponding to a first tissue engaging surface 20. Further, in a non-limiting embodiment, the retaining member 6 includes a biasing element 22.

In a non-limiting embodiment, the tissue retaining element 18 is attached to the rim portion 16 by the biasing element 22 and locking member 12. The biasing element 22 urges the tissue retaining element 18 away from the rim portion 16. The first tissue engaging surface 20 of the tissue retaining element 18 may be attached directly to the biasing element 22. Alternatively, the first tissue engaging surface 20 of the tissue retaining element 18 may be connected to the biasing element 22 by a connecting portion 19, which as shown in FIG. 1, may extend from the first tissue engaging surface 20 towards the rim portion 16.

Generally, when the base 4 and the retaining member 6 are engaged as shown in FIG. 3, an interior area 24 is defined between the base 4 and the retaining member 6 where the first tissue engaging surface 20 and the second tissue engaging surface 14 are facing each other. Prior to this engagement, a tissue sample 2 is placed into this interior area 24 in the desired orientation so that it rests on the second tissue engaging surface 14 of the base 4. Upon engagement of the base 4 with the assembly of retaining member 6 to frame 8, the biasing element 22 urges the first tissue engaging surface 20 of the tissue retaining element 18 towards the second tissue engaging surface 14 of the base 4 to firmly hold the tissue sample 2 in the chosen orientation between the first and second tissue engaging surfaces 14, 20 such that it can be held in position for processing and later be embedded with paraffin or the like.

The biasing element 22 will now be described in additional detail. As noted above the tissue retaining element 18 is attached to the retaining member 6 by at least one biasing element 22. In the illustrated embodiment in FIG. 1, the tissue cassette 1 has four biasing elements 22, where two biasing elements are shown in the Figure on one wall and the other two are on the opposite wall.

As shown in FIG. 1, each biasing element 22 is substantially hinged having an S or Z shape and attach at one end to the tissue retaining element 18 and attach at the other end to the inner surface of the rim portion 16. The biasing element 22 urges the tissue retaining element 18 towards the base 4 to fix the tissue sample 2 between the first and second tissue engaging surfaces 14, 20. Thus, the biasing element 22 can take on any shape that performs this function. For example, a torsion bar or a biasing element having another shape could also be used as discussed in more detail below.

Figure 4:
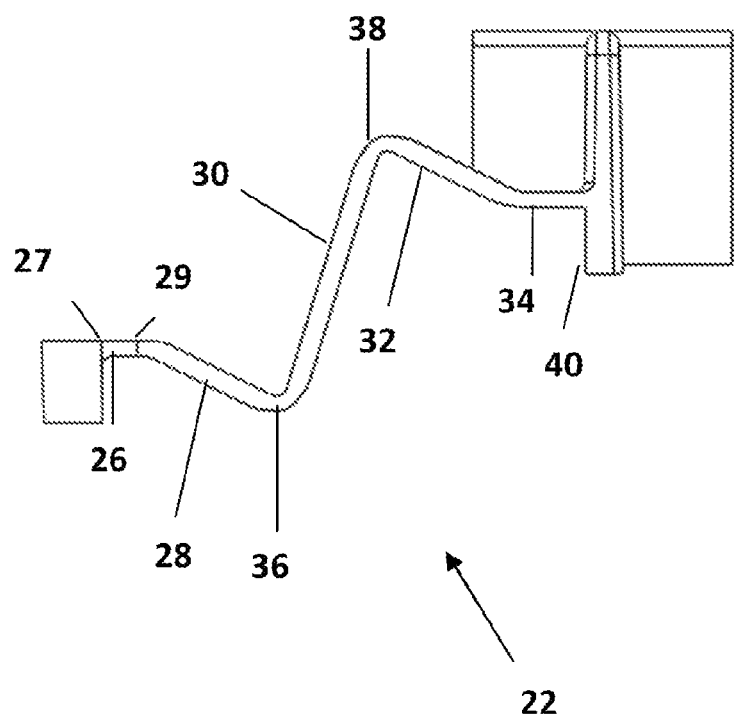
FIG. 4 shows a cut-out section of the biasing element on the tissue cassette of the above embodiment.

In one non-limiting embodiment, as shown in FIG. 4, each biasing element 22 may have a first member 26 with a first end 27 and a second end 29. The first end 27 may be connected to the tissue retaining element 18. Extending downward at an angle from the hinge or second end 29 of the first member 26 is a first angled member 28. A second angled member 30 is connected to the first angled member 28 by a first curved hinged point 36. The second angled member 30 extends upwardly from the first angled member 28 at an angle; and in a non-limiting embodiment, the second angled member 30 and the first angled member 28 form an angle less than 90°. Extending downwardly from the second angled member 30 is a third angled member 32. The second angled member 30 and the third angled member 32 are connected by a second curved hinge point 38. In a non-limiting embodiment, the third angled member 32 and the second angled member 30 form an angle less than 90°. Further, in a non-limiting embodiment, the third angled member 32 and the first angled member 28 form an angle less than 90°. A second member 34 connects to the third angled member 32 at a hinge point and extends substantially parallel to the tissue retaining element 18. The second member 34 attaches to the rim portion 16 of the retaining member 6 in a non-limiting embodiment.

The biasing element 22 has a particular flexibility to ensure that the tissue sample 2 is held between the first and second tissue engaging surfaces 14, 20, on the one hand, but to also ensure that the tissue sample 2 withstands any permanent damage during processing. The preferred maximum biasing force depends on the tissue sample and is up to about 2.5N. Typically, biasing force may be measured using a force gauge.

More detail with respect to the retaining member 6 will now be provided with reference to FIGS. 1 and 2. In this exemplary embodiment, the retaining member 6 includes the rim 16, the biasing element 22, the connector 19, the retaining element 18 and the first tissue engaging surface 20. The rim 16 has four walls and a substantially rectangular shape. On the inside of the rim 16 one end of the biasing member 22 is attached. One end of the biasing member 22 attaches to the tissue retaining element 18 at either the connector 19 or the first tissue engaging surface 20. The tissue retaining element 18 of the retaining member 6 has a connector 19 and a first tissue engaging surface 20 with a substantially planar mesh portion 42. In this embodiment the mesh portion 42 is rectangular in shape, but the shape is not limiting and the mesh portion can be a variety of shapes. The mesh portion 42 of the first tissue engaging surface 20 has a plurality of perforations 44 or cut-outs. When the mesh portion 42 is urged against the tissue sample 2 it holds the tissue sample 2 in place and allows reagents, or the like, to flow to the tissue sample 2 through the perforations 44 in the mesh portion 42. The perforations 44 are sized to allow the flow of fluid to the tissue sample 2 on the one hand, but to prevent the escape of the tissue sample 2 on the other hand. Thus, the perforations 44 in the mesh portion 42 may be sized according to the size of the tissue sample 2. Further, the first tissue engaging surface 20, may alternatively be solid and have no holes on the surface while still allowing the agent to flow underneath the first tissue engaging surface 20 from the periphery.

Figure 5:
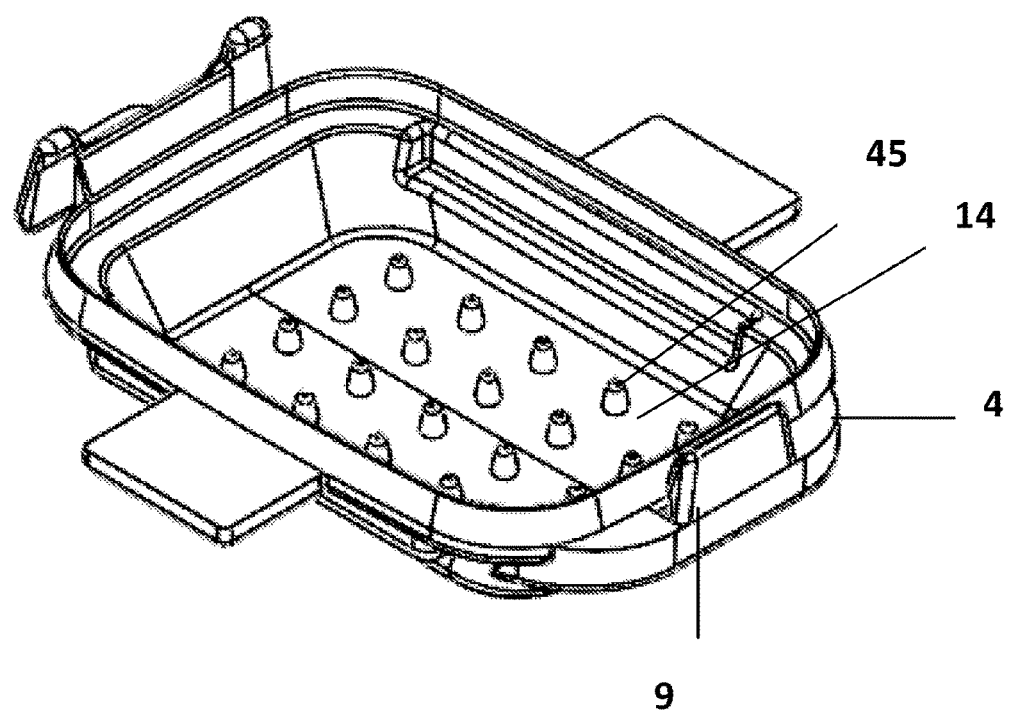
FIGS. 5-6 show an alternate embodiment of the base.

The first tissue engaging surface 20 of the tissue retaining element 18, and/or the second tissue engaging surface 14 may contain topography to help orient the tissue sample. For example, the tissue engaging surfaces 14, 20 may contain prongs 45, ridges, hooks, or the like as shown on a second tissue engaging surface 14 in FIG. 5. In certain non-limiting embodiments, the tissue retaining element 18 has a semi-rigid structure to secure the tissue sample 2 without deformation; however, the tissue retaining element 18 may also have a rigid structure without changing the scope of the invention.

Further as shown in FIG. 1, the tissue retaining element 18 may also have protrusions 46 which extend downwardly from the tissue retaining element 18 towards the base 4. The protrusions 46 act as dead stops to prevent the tissue retaining element 18 from pushing down too hard against the tissue sample 2.

Additionally, in a non-limiting embodiment, the retaining member 6 may have handles 48 which function as grips for the lab technician when transporting the tissue cassette 1. Further, in a non-limiting embodiment, the retaining member 6 may contain a wire 47 which extends the length of the retaining member 6 and can be used for retraction when separating the retaining member 6 from the base 4.

The base 4 will now be described with reference to FIG. 1. As discussed above, the tissue cassette 1 has a base 4 which supports the tissue sample 2 and holds the paraffin for embedding. The base 4, as shown in FIG. 1, has a generally rectangular shape with four side walls and a depressed bottom planar surface, referred to as the second tissue engaging surface 14. The base 4 has a rectangular shape depicted in the Figures; however, it is not limited to this shape and a different shape could be used without changing the scope of the invention. The base 4 is preferably solid so that it can hold the paraffin for embedding. The walls of the base 4 are preferably tapered inward to improve the ease at which the base can be removed from the paraffin after the embedding process.

Figure 6:
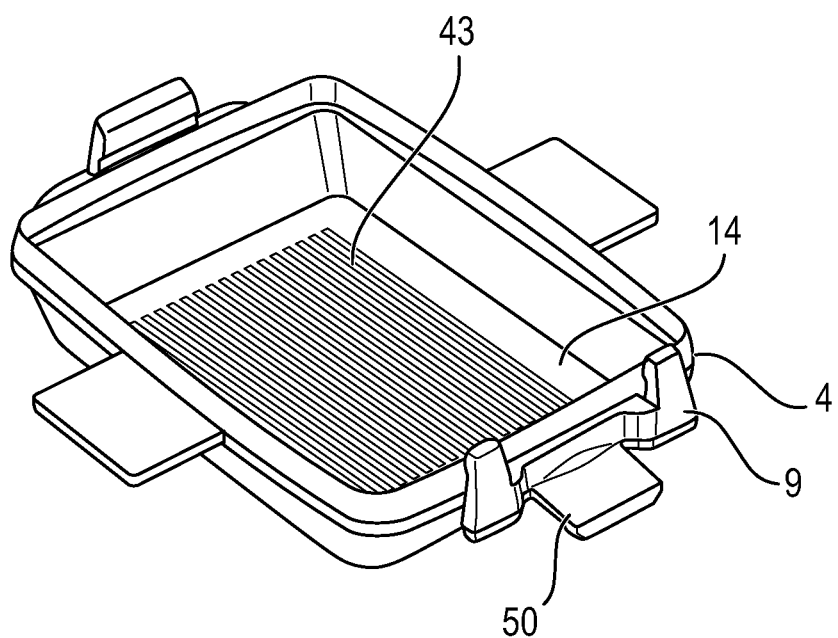

As shown in FIG. 1, the base 4 has a solid, smooth bottom. However, in some embodiments the base 4 may have grooves or some other texture. As an example, the second tissue engaging surface 14 of the base 4 may have flow channels 43, depicted in FIG. 6, to assist in retaining the tissue sample 2 and improving fluid flow, without changing the scope of the invention. In an alternative embodiment, the base 4 may be have a second depressed bottom for receiving the tissue sample such that the second depressed bottom creates an interior subsection with an area smaller than the interior area 24. The second depressed bottom 49 may be used for tissue samples 2 smaller in size.

In certain embodiments, the base 4 may also have drainage guides 50. The drainage guides 50 help to wick away the paraffin and to channel the paraffin away from the tissue cassette 1 after the tissue sample 2 has been embedded. The drainage guides 50 extend out from the outer peripheral of the base. In the embodiment shown in FIG. 6, the drainage guides 50 extend from one of the two end walls of the base; however the drainage guides 50 could extend from any wall on the base 4.

As noted above, in some embodiments a frame 8 is placed around the outside perimeter of the retaining member 6 and functions to secure the retaining member 6 to the base 4. The frame 8 may also be used as a means for identifying the tissue sample. As shown in FIG. 1, the frame 8 has a substantially rectangular shape with one end have an angled projection with an angled face 52. As shown in FIG. 1, a label 54 may be placed on the angled face 52 to identify the tissue sample 2. The labels 54 are described in more detail below. In this embodiment, the angle of the planar face is about 45 degrees, but the invention is not limited in this respect. The angled face 52 can be configured to receive a label such that the label 54 clicks into the angled face 52 of the frame 8. Alternatively, the frame 8 may have a textured surface and be put through an inkjet printing system, such as Leica IPC ink jet printer. In this instance, the tissue cassette 1 can be assembled after printing or the base 4 along with the frame 8 can be configured to be sent through the printer.

In a non-limiting embodiment, the frame 8 and the retaining member 6 are not easily removed so that once the tissue cassette 1 is used, the label 54 on the frame 8 will remain matched with the tissue sample 2 contained in the tissue cassette 1. In certain embodiments, frame 8 has a locking projections 12 which projects from the inside the perimeter of the frame 8, shown in FIG. 1. The locking projections 12 attach with an engaging portions 55 on the outer perimeter of the rim portion 16 on the retaining member 6 to secure the frame 8 to the retaining member 6. Once the frame 8 is connected to the base 4 using this locking arrangement, it is difficult to separate them.

The base 4 includes a latching member 9 which acts as a clip or lock to hold the base 4 to the frame 8. Alternatively, if a frame 8 is not used, the latching member 9 can lock the base 4 to the retaining member 6.

As shown in FIG. 2, the latching member 9 is connected to a releasing member 60. The latching member 9 is flexibly attached to the base 4. When the latching member 9 is engaged, the latching member 9 attaches to the clip surfaces 56 on the outer perimeter of the frame 8. The latching member 9 locks the base 4 to the frame 8 which is attached to the retaining member 6. In this way, a sealing member 10 connects the latching member 9 to the base 4 to form a seal between the surfaces on the perimeter of the base 4 and the frame 8 to sufficiently prevent paraffin from leaking during embedding. In a non-limiting embodiment a gasket may be used as the sealing member 10 to help seal the base 4 and the frame 8. The latching member 9 is disengaged by pressing downward on the releasing member 60. When the releasing member 60 is pressed, the latching member 9 moves away from the base 4 and disengages from the clip surfaces 56. In the embodiment described above, the sealing member 10 extends from the base 4, but the sealing member 10 may also extend from the retaining member 6 or the frame 8.

An important aspect of tissue sample analysis is properly keeping track of tissue samples. In some embodiments, the tissue cassette 1 includes a label 54 or ID tag as shown in FIG. 1. The label can 54 be located anywhere on the tissue cassette 1, but is preferably located on the frame 8. In some embodiments, more than one tag may be present. When more than one tag is present, the tags can be physically separated or located together.

The label 54 may be a computer or human readable tag including, but not limited to, labels having an incorporated RFID, labels having an incorporated one-dimensional barcode (1-D barcode), labels having an incorporated two-dimensional barcode (2-D barcode), and labels having an incorporated three-dimensional barcode (3-D barcode). However, the computer readable label is not limited to RFID, 1-D barcode, 2-D barcode, or 3-D barcode labels and may include any type of label readable by a computer as would be apparent to a person of ordinary skill in the art.

In some embodiments, a label 54 is present that may be sensitive to changes to the sample or itself. For example, a label 54 may be present that changes physical (i.e. color) or chemical (i.e. redox, conjugation, etc.) properties during fixation of the sample. Similarly, a label 54 may be present that is sensitive to the processing steps which precede embedding (i.e. dehydration). Alternatively, a label 54 may be present that is sensitive to the embedding step (i.e. infiltration of paraffin). The label 54 may have a property that changes incrementally or switches when the step is complete. In this way, the technician, or an automated system, will be able to determine when the sample has finished one step before another is started.

The tissue cassette 1 can be made from various materials and the same or different materials can be used for the retaining member 6, including the tissue retaining element 18, the first tissue engaging surface 20, the mesh portion 42, and the base 4. Examples of materials used include: an acetal copolymer, Teflon, polypropylene, and stainless steel. In a non-limiting embodiment, the acetal copolymer is DELRIN 900. In a non-limiting embodiment, the base 4 is made out of a polypropylene material so that the base 4 does not attach to the paraffin after the tissue sample 2 is embedded. In a non-limiting embodiment, the sealing member 10 is made out of a polypropylene material.

In a non-limiting embodiment, the tissue cassette, including the base, the retaining member, and/or the frame, may be produced from a material lacking any dye or coloring. The lack of color may allow the technician to view the tissue sample in the tissue cassette and ensure that the tissue sample has remained in its desired orientation after embedding. In these embodiments, the tissue cassette, including the base, the retaining member, and/or the frame may be at least at least opaque or clear.

Figure 7:
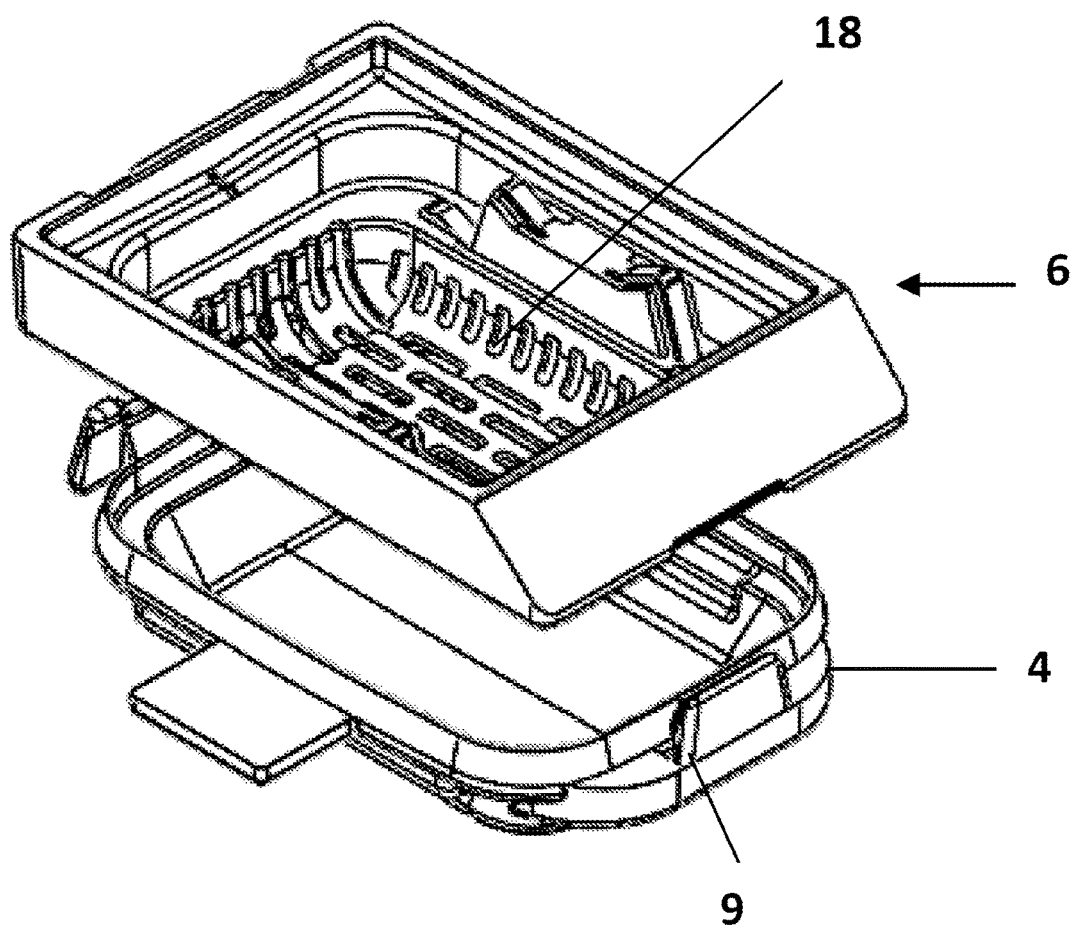
FIG. 7 is an exploded view of a tissue cassette according to another embodiment in a non-assembled state.

FIG. 7 shows a further embodiment of the tissue cassette 1. This embodiment is different from the previously described embodiments in the following respects. First, instead of having a separate frame, the frame of this embodiment is integrally incorporated into the retaining member 6. Second, the tissue retaining element 18 is shaped more like a basket, having four side walls. Lastly, the latching member 9 is formed on an end wall of the base 4, but has the same function of locking the base 4 to the retaining member 6. Other than these differences noted, the embodiment shown in FIG. 7 has the same configuration and tracks the same structure as discussed above.

Figure 8:
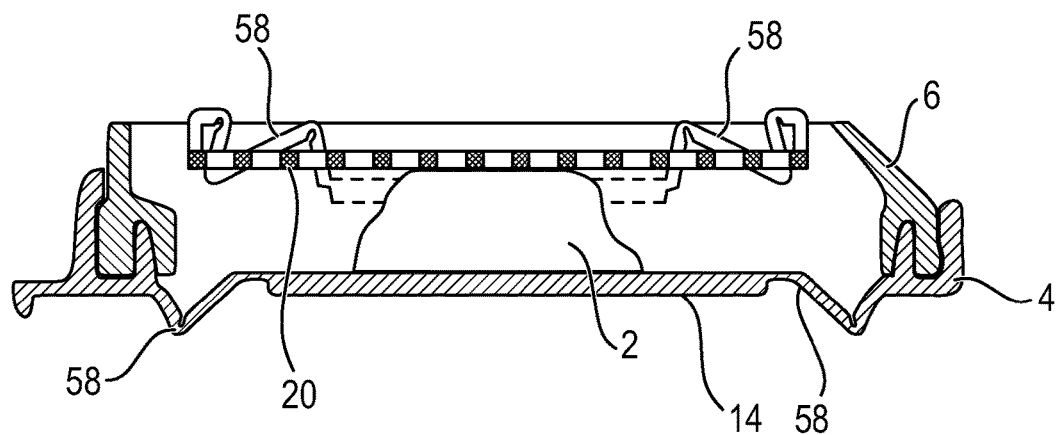
FIG. 8 is an interior side view of a tissue cassette according to another embodiment in an assembled state with the tissue sample.

FIG. 8 shows a further embodiment of the tissue cassette 1. This embodiment is different from the previously described embodiments in that in this embodiment, a biasing member 58 may be provided on either the base 4 or the retaining member 6 or both, along with the biasing element 22 as described in the above embodiments. In this embodiment, the biasing member 58 on the retaining member 6 may be pushing down and the biasing member 58 attached to the base 4 may provide a biasing force to move the second tissue engaging surface 14 away from the first tissue engaging surface 20. Furth, the biasing member 58 attached to the retaining member 6 may permit the retaining member 6 to move away from the base 4 in response to the biasing force provided by the base 4. Similarly, the biasing member 58 attached to the base 4 may permit the base 4 to move away from the retaining member 6 in response to the biasing force provided by the retaining member 6. In this embodiment, the tissue sample container 1 is stable when either the biasing member 58 attached to the retaining member 6 or biasing member 58 attached to the base 4 is applying a biasing force, or when both are applying or not a biasing force.

For example, in this non-limiting embodiment, the biasing member 58 on the base 4 may be used only to enable the releasing of the force that is applied by the biasing member 58 on retaining member 6. As an example, in this embodiment, the tissue cassette 1 provides a two position floor. The first position is when the biasing member 58 on the base 4 compresses the second tissue engaging surface 14 upwardly such that the tissue engaging surface is compressed up towards the retaining member 6 to compress the tissue sample 2. The second position is when the force of the biasing member 58 on the base is released so that the second tissue engaging surface 14 is moves downwardly. In this way, the second tissue engaging surface 14 retracts away from the tissue 2, such that the floor of the base retracts, similar to the first tissue engaging surface 20 of the previous embodiments retracting towards and away from the tissue sample 2. Other than these differences noted, the embodiment shown in FIG. 8 has the same configuration and tracks the same structure as discussed above.

Figure 9A:
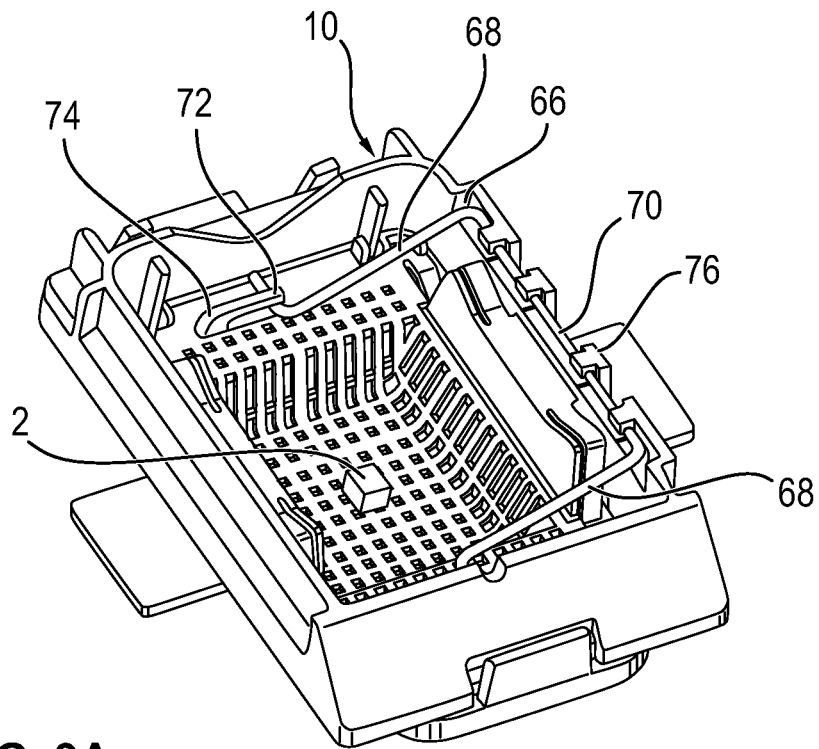
FIGS. 9A-9B, 10A-10B and 11A-11B show the tissue cassette according to alternative embodiments.
Figure 9B:
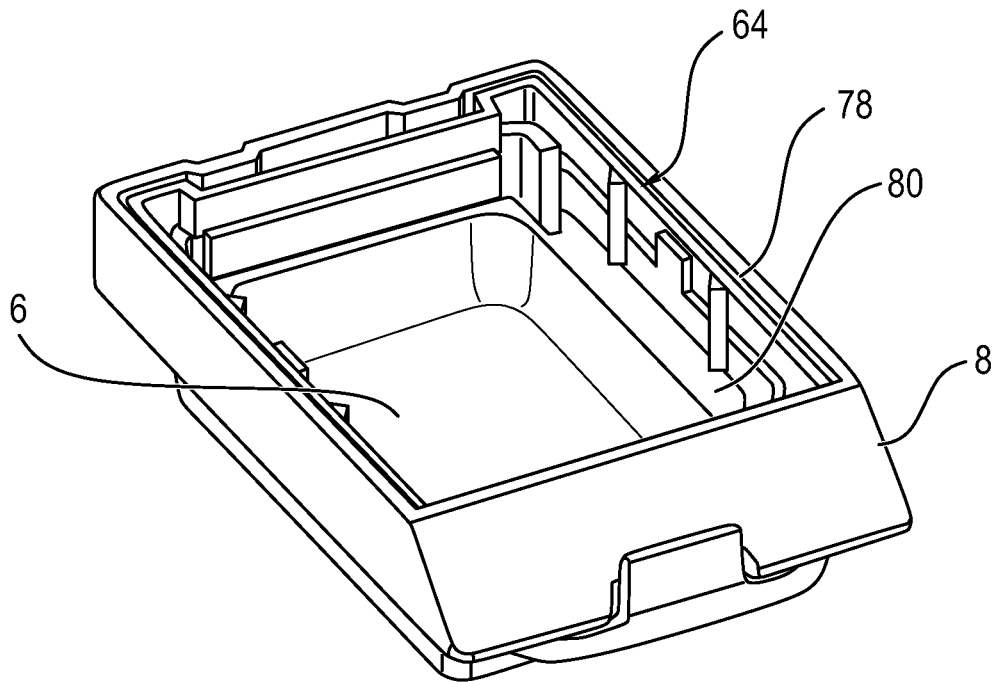

FIGS. 9-11 illustrate alternative embodiments of the invention which are directed towards maintaining parallel configuration of the first tissue engaging 20 surface when it urges towards the second tissue engaging 14 or when it retracts away from the second tissue engaging surface 14. FIGS. 9A and 9B illustrate examples of guiding members 64 which assist the first tissue engaging surface 20 to maintain parallel configuration to the base 4 as it urges towards to the base 4. FIG. 9A illustrates a wire guide 66 used as the guiding member. In FIG. 9A the wire guide 66 is attached to the retaining member 10. The specific location is not limited; the wire guide 66 could be attached anywhere on the retaining member 10 including directly on the first tissue engaging surface 20. In the example shown in FIG. 9A, the wire guide 66 has a substantial U-shape with two parallel members 68 connected by a cross member 70. Projections 72 extend out from one end of each of the parallel members 68 to attach to clips 74 in the center of the retaining element 18. The wire guide 66 may pivot at the clips 74 such that when a downward force is applied to the wire guide 66 the retaining element 18 urges towards the tissue sample 2 along a central axis of the clips 74 to maintain a parallel configuration of the tissue retaining element 18 and the first tissue engaging surface 20 with the base 4. The cross member 70 can be locked into place by cross member clips 76 attached to the frame 8 or the retaining member 10.

FIG. 9B shows pillars 78 as guiding members 64. In this embodiment, pillars 78 extend vertically upward from the interior of the frame 8. Further, the side walls of the retaining member 6 have at least one cut-out 80 which are shaped to receive the pillars 78. Accordingly, the retaining element 18 can maintain a parallel configuration with the base 4 when it moves towards the tissue sample 2 or away from the tissue sample 2.

In addition to the guiding members 64 discussed above, there are alternative designs relating to the biasing element 22 which help to maintain the parallel configuration of the first tissue engaging surface 20 to the base 4. The biasing element 22 described above is one example of a means to hold the tissue sample 2 in the tissue cassette 1. As noted above, any design that performs the function of urging the first tissue engaging surface 20 against the second tissue engaging surface 14 can be used. Alternate embodiments of the biasing element 22 to remain parallel configuration of the first tissue engaging surface 20 with the base 4 are shown in FIGS. 10-11.

Figure 10A:
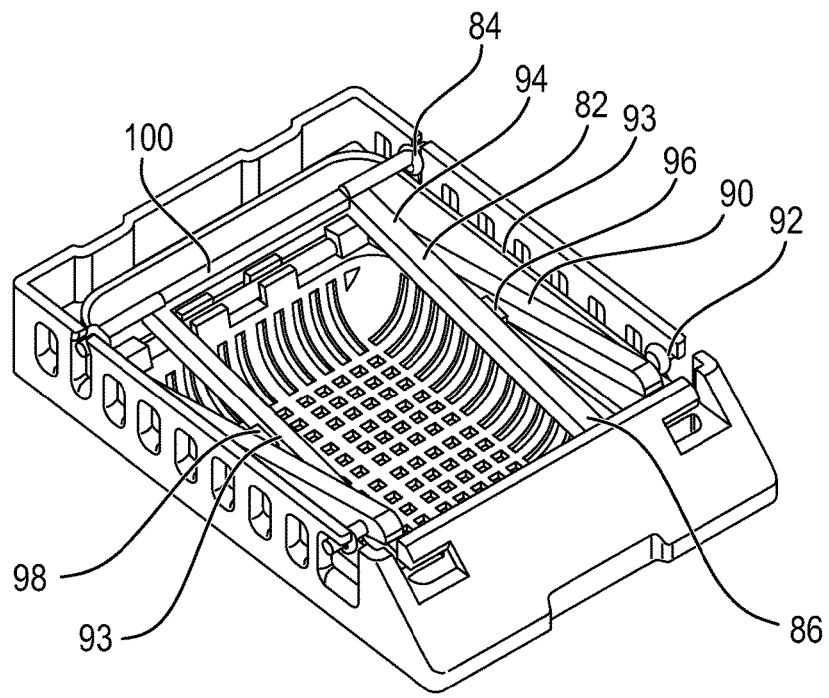
Figure 10B:
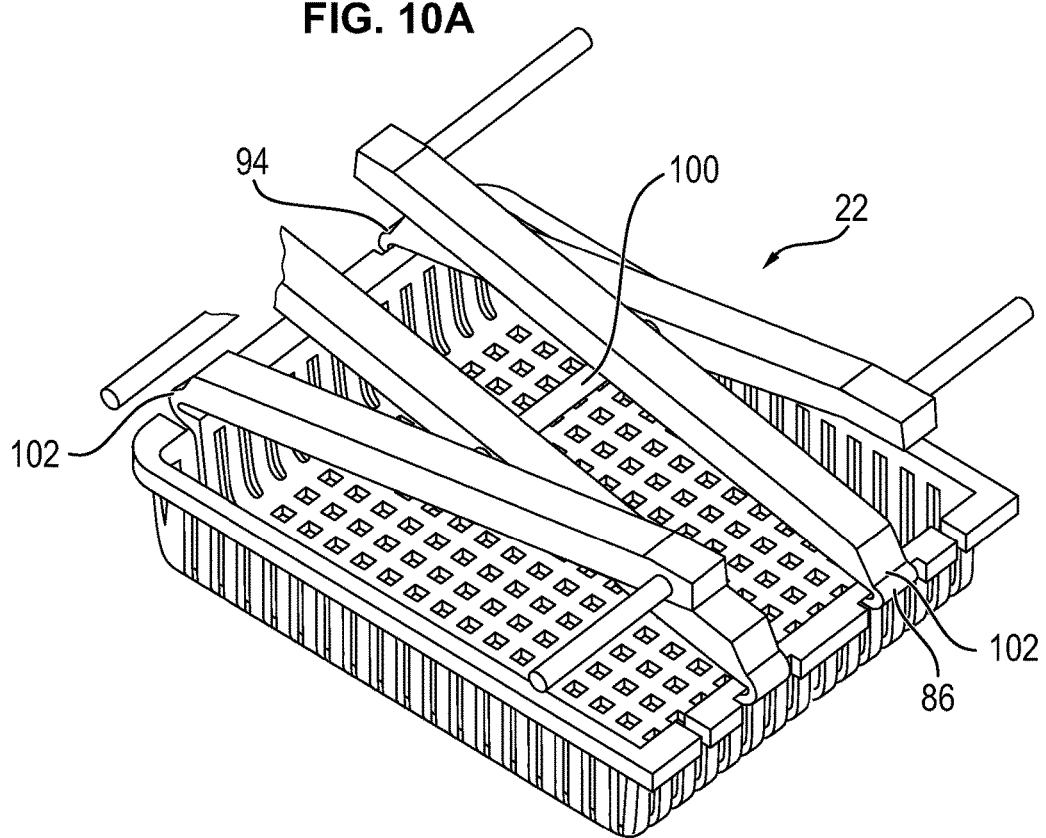

FIG. 10A and FIG. 10B illustrate an alternate embodiment to the biasing element 22. In these examples, the biasing element 22 includes two angled members. The first angled member 82 is fixed to the retaining member 6 at a fixed point 84 and angles downward from the fixed point 84 and attaches to the retaining element 18 at a first moving point 86. The second angled member 90 attaches to the retaining member 6 at a sliding point 92. The second angled member 90 is not fixed at the sliding point 92 and can slide against an inner ledge 93 of the retaining member 6 in a direction parallel to the second tissue engaging surface 14. The second angled member 90 extends downward from the sliding point 92 and attaches to the retaining element 18 at a second moving point 94. The first angled member 82 and the second angled member 90 are angled such that the members cross substantially in the center of each member at a hinge point 96.

In this embodiment, the first angled member 82 is fixed to the retaining member 6 at the fixed point 84. The second angled member 90 is attached to the retaining member 6 at the sliding point 92. Thus, the second angled member 90 can slide only in the direction parallel to the second tissue engaging surface 14. Accordingly, as the first angled member 82 and the second angled member 90 urge the first tissue engaging surface 20 towards the tissue sample 2, the first moving point 86 and the second moving point 94 move towards the tissue sample 2 while keeping the first tissue engaging surface 20 parallel to the base 4, for example.

In certain embodiments as shown in FIG. 10A, the pair of angled members 82, 90 cross at the hinge point 96 and are connected by a torsion bar 98. As shown in FIG. 10A, the pair of angled members may be provided on each side of the tissue cassette 1. Accordingly, the tissue cassette 1 has two pairs of angled members, although the number of pairs of angled members is not limiting. The two pairs of angled members are attached by a connecting bar 100. The connecting bar 100 can connect the two pairs of angled members at any point along the members.

FIG. 10B shows an alternate embodiment, where the biasing element 22 is provided by a flexible hinges 102 at the connection points between the first and second angled member and the retaining element 18. That is, there are flexible hinges 102 at the first moving point 86 or the second moving point 94. Similar to the embodiment described in 10A, the first tissue engaging surface 20 can maintain a parallel configuration to the base 4 while moving towards the tissue sample 2. The flexible hinges 102 allow pair of angled members to flex under pressure.

Figure 11A:
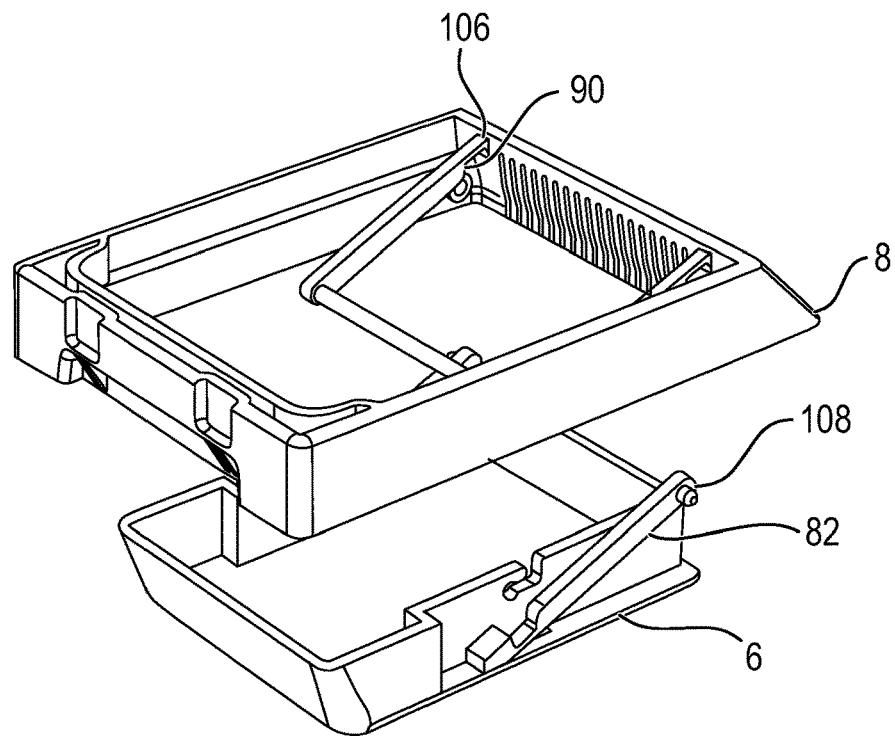
Figure 11B:
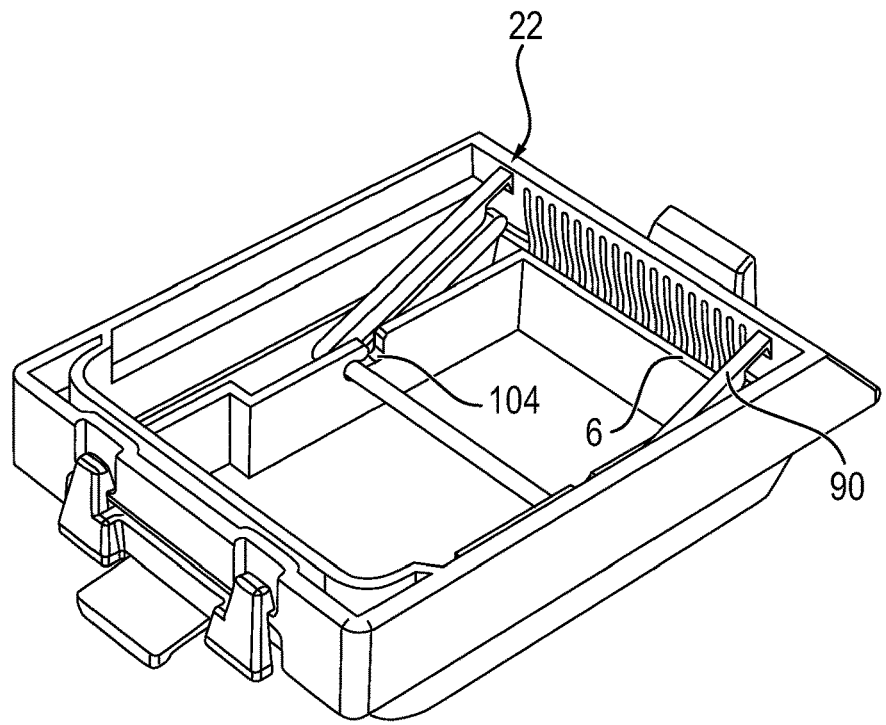

Alternatively, as shown in FIGS. 11A and 11B, the biasing element 22 can comprise two angled members extending in a parallel direction. The first angled member 82 is attached to the retaining member 6 and the second angled member 90 is attached to the frame 8. In FIG. 11A, the frame 8 and the second angled member 90 are placed over the retaining member 6 and the first angled member 82 so that the first angled member 84 and the second angled member 90 are adjacent to each other and extend in parallel directions.

The second angled member 90 contacts to the retaining member 6 at a hinge 104 and attaches to the frame a first pivot point 106. The first angled member 82 attaches to the frame 8 at a second pivot point 108. Accordingly, the retaining element 18 may be moved towards the tissue sample 2 in a parallel manner by the first angled member 82 pivoting about the second pivot point 108 and the second angled member 90 rotating about the first pivot point 106. When the two angled member rotate about their respective pivot points the retaining element 18 moves in a substantially a parallel direction. Similar to the embodiment describe with respect to FIGS. 11A and 11B, a torsion bar may be provided in this embodiment. The torsion bar may be located at any point where the two pair of angled members connect.

An example of the use of the tissue cassette 1 in the analysis process will now be described. The tissue sample 2 is extracted and sent to a lab for analysis. In certain non-limiting embodiments, a gel may be placed on a tissue engaging surface, for example the second tissue engaging surface 14 as an adhesive to further secure the tissue sample 2. An example of gel for use include agarose, agarose derivatives, modified agarose, low melt agarose, hydroxyethylagarose, low molecular weight agarose, agar, alginates, dextran, mannan, pectin, Ghatti gum and cellulose including hydroxypropylcellulose, histogel, hydrogel or combinations thereof, Then the tissue sample 2 is orientated and placed onto the second tissue engaging surface 14 of the base 4 of the tissue cassette 1. The retaining member 6 is then placed over the base 4 and secured in place by the frame member 8. Once the cassette is assembled, the biasing element 22 in the retaining member 6 is deflected to urge the tissue retaining element 18 of the retaining member 6 towards the tissue sample 2 such that the tissue sample 2 is held in its oriented position.

The tissue cassette 1 is then processed and exposed to a molten substrate. In a non-limiting embodiment, the tissue cassette 1 is filled with paraffin. The molten paraffin infiltrates the tissue cassette 1 and enters the interior area 24 to embed the tissue sample 2 in its oriented position. The paraffin is then cooled such that it hardens at which point the tissue sample is embedded in a paraffin block and ready for sectioning. The base 2 is disengaged from the frame 8 such that the paraffin block including the tissue sample is exposed, resting on the first tissue engaging surface 20 of the retaining member. The paraffin block including the tissue sample can then be sectioned using a microtone. After the tissue sample 2 is sliced it is ready to be placed on a microscope slide for further processing and inspection.

Although a few example embodiments have been shown and described, these example embodiments are provided to convey the subject matter described herein to people who are familiar with this field. It should be understood that the subject matter described herein may be embodied in various forms without being limited to the described example embodiments. The subject matter described herein can be practiced without those specifically defined or described matters or with other or different elements or matters not described. It will be appreciated by those familiar with this field that changes may be made in these example embodiments without departing from the subject matter described herein as defined in the appended claims and their equivalents. Further, any description of structural arrangement of components or relationship there between is merely for explanation purposes and should be used to limit an example embodiment.

Aspects related to the example embodiment have been set forth in part in the description above, and in part should be apparent from the description, or may be learned by practice of embodiments of the application. Aspects of the example embodiment may be realized and attained using the elements and combinations of various elements and aspects particularly pointed out in the foregoing detailed description and the appended claims. It is to be understood that both the foregoing descriptions are an example and are explanatory only and are not intended to be limiting.

What is claimed is:

1. An apparatus for holding a tissue sample comprising,
a retaining member including a tissue retaining element having a first tissue engaging surface and at least one biasing element, the tissue retaining element being moveably attached to the retaining member by said biasing element; and
a base comprising a second tissue engaging surface and configured to engage the retaining member to form an interior area with the first and second tissue engaging surfaces facing each other,
wherein the retaining member is removably attached to the base, wherein the at least one biasing element urges the tissue retaining element and the first tissue engaging surface toward the second tissue engaging surface to retain the tissue sample between the first tissue engaging surface and the second tissue engaging surface in the interior area, and wherein the base comprises a latching member configured to latch onto a side of the retaining member facing opposite of the base such that the at least one biasing element is elastically deformed against the tissue retaining element.

2. The apparatus according to claim 1, wherein the retaining member comprises two biasing elements for moveably supporting the first tissue engaging surface such that the first tissue engaging surface is urged toward the second tissue engaging surface.

3. The apparatus according to claim 1, wherein the biasing element is configured to provide a maximum biasing force less than or equal to 2.5 Newtons.

4. The apparatus according to claim 1, wherein the biasing element is substantially hinged.

5. The apparatus according to claim 2, wherein the retaining member comprises a rim portion and the tissue retaining element on which the first tissue engaging surface is defined.

6. The apparatus according to claim 1, further comprising a latching member formed on one of the retaining member and the base to releasably hold the retaining member and the base.

7. The apparatus according to claim 6, wherein the latching member is flexibly attached to the base and extending upwardly therefrom for engaging a frame attached to the retaining member.

8. The apparatus according to claim 7, further comprising a releasing member connected to the latching member, wherein the latching member disengages from the frame when a force is applied to the releasing member.

9. The apparatus according to claim 8, further comprising a sealing member that forms a liquid seal between the retaining member and the base.

10. The apparatus according to claim 1, wherein a label is attached at least one of a frame surrounding the retaining member, the retaining member, and the base.

11. The apparatus according to claim 10, wherein the label comprises a computer readable Label.

12. The apparatus according to claim 11, wherein the computer readable Label comprises at least one of a readable writable label a two-dimensional barcode and a three-dimensional barcode.

13. The apparatus according to claim 12, wherein the computer readable Label contains information unique to the tissue sample.

14. The apparatus according to claim 13, wherein the information unique to the tissue sample includes one or more of patient identification information, sample collection site location information, collection temperature, collection time, and collection conditions.

15. The apparatus according to claim 1, wherein the first tissue engaging surface of the retaining member is perforated having a plurality of holes formed therethrough.

16. The apparatus according to claim 1, wherein the second tissue engaging surface of the base is perforated having at least one hole formed therethrough.

17. The apparatus according to claim 1, wherein the second tissue engaging surface of the base is solid.

18. The apparatus according to claim 1, wherein at least one flow channel is formed in the second tissue engaging surface to allow fluid to flow underneath the tissue sample held between the first tissue engaging surface and the second tissue engaging surface.

19. The apparatus according to claim 1, wherein at least one protrusion is provided on one of the first tissue engaging surface and the second tissue engaging surface to prevent at least a portion of the first tissue engaging surface from contacting the second tissue engaging surface.

20. The apparatus according to claim 19, wherein the at least one protrusion extends away from the one of the first tissue engaging surface and the second tissue engaging surface to contact and support the other of the first tissue engaging surface and the second tissue engaging surface.

21. The apparatus according to claim 1, wherein the retaining member is formed of an acetal copolymer.

22. The apparatus according to claim 21, wherein the acetal copolymer is DELRIN 900.

23. The apparatus according to claim 1, wherein the base is formed of polypropylene.

24. The apparatus according to claim 9, wherein the sealing member is formed of polypropylene.

25. An apparatus for holding a tissue sample comprising,
a retaining member having an tissue retaining element and at least one biasing element, the tissue retaining element being moveably attached to the retaining member by said biasing element; and
a base configured to engage the retaining member to form an interior area,
wherein the retaining member is removably attached to the base,
wherein the at least one biasing element urges the tissue retaining element toward the base to retain the tissue sample therebetween in the interior area, and
wherein the base comprises a latching member configured to latch onto a side of the retaining member facing opposite of the base such that the at least one biasing element is elastically deformed against the tissue retaining element.

26. An apparatus for holding a tissue sample comprising,
a retaining member having a first tissue engaging surface;
a base having a second tissue engaging surface; and
at least one biasing element,
wherein at least one of the first tissue engaging surface and the second tissue engaging surface is moveably attached to at least one of the retaining member and the base by said biasing element,
wherein the base and the retaining member are configured to removably engage each other to form an interior area with the first and second tissue engaging surfaces facing each other,
wherein the at least one biasing element urges at least one of the first tissue engaging surface and the second tissue engaging surface to retain the tissue sample therebetween in the interior area, and
wherein the base comprises a latching member configured to latch onto a side of the retaining member facing opposite of the base such that the at least one biasing element is elastically deformed against the tissue retaining element.

27. The apparatus according to claim 26, wherein the retaining member has at least two biasing elements,
wherein the at least two biasing elements urge the first engaging surface of the retaining member toward the second engaging surface of the base and maintain the engaging surfaces in a substantially parallel configuration.

28. The apparatus according to claim 27, further comprising a guiding member to maintain the engaging surfaces in a substantially parallel configuration.

29. The apparatus according to claim 28, wherein the guiding member is at least one pillar extending along an inside perimeter of the interior area,
wherein the retaining member has cut-outs configured to receive the pillars.

30. The apparatus according to claim 29, wherein the guiding member is a wire guide attached to the retaining member.

31. The apparatus according to claim 27, wherein the biasing element comprises:
a pair of angled members connected by a hinge,
wherein the pair of angled members extend in opposite directions to form a crossed configuration,
wherein at least one of the pair of angled members is slidably connected to the retaining member by a sliding pin connection which allows the at least one pair of angled members to slide along the retaining member, and
wherein the hinge allows relative rotation between the pair of angled members to maintain the engaging surfaces in substantially parallel configuration.

32. The apparatus according to claim 31, wherein the hinge comprises a torsion biasing element.

33. The apparatus according to claim 27, wherein each biasing element comprises:
a pair of angled members, extending substantially parallel to each other,
wherein each of the pair of angle members are rotatably connected to the first tissue engaging surface at a first end,
wherein each of the pair of angled members are rotatably connected to the retaining member at a second end.

34. The apparatus according to claim 33, wherein the first of the pair of angled members is connected to the second of the pair of angled members by a torsion biasing element that allows relative rotation between the pair of angled members.

* * * * *